United States Patent [19]
Kim et al.

[11] Patent Number: 5,856,141
[45] Date of Patent: Jan. 5, 1999

[54] PROCESS FOR MANUFACTURING CYCLOSPORIN A BY HIGHLY PRODUCTIVE FUSANT STRAIN

[75] Inventors: Jung Woo Kim, Seoul; Kwang Moo Lee, Anyang; Byoung Tack Choi; Jin Man Lee, both of Seoul; Nak Kyu Sung, Euwang; Kyeong Bok Min, Seoul, all of Rep. of Korea

[73] Assignee: Chong Kun Dang Corp., Seoul, Rep. of Korea

[21] Appl. No.: 817,392

[22] PCT Filed: Oct. 16, 1995

[86] PCT No.: PCT/KR95/00131

§ 371 Date: Apr. 18, 1997

§ 102(e) Date: Apr. 18, 1997

[87] PCT Pub. No.: WO96/12032

PCT Pub. Date: Apr. 25, 1996

[30] Foreign Application Priority Data

Oct. 18, 1994 [KR] Rep. of Korea .................. 26689/1994

[51] Int. Cl.$^6$ ...................................... C12P 21/04
[52] U.S. Cl. ..................... 435/71.1; 435/71.3; 435/42; 435/171; 435/172.2; 435/254.1; 435/911; 530/317; 530/321
[58] Field of Search ................................ 435/71.1, 71.3, 435/911, 254.1, 171, 172.2, 42; 530/317, 321

[56] References Cited

U.S. PATENT DOCUMENTS

| | | | |
|---|---|---|---|
| 4,943,529 | 7/1990 | Van Den Berg et al. | 435/172.3 |
| 5,156,960 | 10/1992 | Bokany et al. | 435/71.1 |
| 5,244,790 | 9/1993 | Kim et al. | 435/42 |
| 5,256,547 | 10/1993 | Rudat et al. | 435/254.1 |
| 5,318,901 | 6/1994 | Patchett et al. | 435/71.1 |
| 5,639,852 | 6/1997 | Rich et al. | 530/321 |

OTHER PUBLICATIONS

Traber et al., "Neu Cyclosporine aus *Tolypocladium inflatum*) Die Cyclosporin K–Z", *Helyetica Chimica Acta* 70:13–35 (1987).

Borel, "Editorial: Ciclosporin and Its Future", *Prog. Allergy* vol. 38:9–18 (1986).

Rüegger et al., "Cyclosporin A, ein Immunosuppresive Wirksamer Peptidmetabolit aus *Trichoderma Polysporum* (Link ex Pers.)", *Helvetica Chimicia Acta* 59(4):1075–1092 (1976).

Kobel et al., "Directed Biosynthesis of Cylosporins", *European J. Appl Microtechnol.*, 14:237–240 (1982).

Anné et al., "Induced Fusion of Fungal Protoplasts Following Treatment with Polyethylene Glycol", *J. Gen. Microbiol.* 92:413–417 (1976).

Peberdy et al., "Regeneration of Aspergillus nidulans Protoplasts", *J. Gen. Microbiol.* 69:325–330 (1971).

*Primary Examiner*—Herbert J. Lilling
*Attorney, Agent, or Firm*—Jacobson, Price, Holman & Stern PLLC

[57] ABSTRACT

The present invention relates to a process for making a highly productive fusant of *Tolypocladium inflatum*, a producing strain of cyclosporin A with immunosuppressive properties wherein the selection of the fusant KD461, designed to produce a large amount of cyclosporin A, was made available by the following steps of: developing amino acid-dependent mutants of *Tolypocladium inflatum*, wild strain isolated from soil, which mutants are induced by UV radiation; conjugating L-valine-dependent and L-leucine-dependent mutants to promote the demand and utility of L-valine and L-leucine, precursors of cyclosporin A, together with an organic nitrogen-source. The fusant KD461 produced has the following characteristics in comparison with wild strain: 1) it is slow growing in a solid malt-yeast extract agar medium, b) the surface of the colony is light grey in color and is therefore darker than the mild strain, c) the backside of the colony is dark brown, and d) in a liquid medium it has short and thick hyphae with many arthrospore.

5 Claims, 2 Drawing Sheets

PROCESS FOR MANUFACTURING CYCLOSPORIN A BY HIGHLY PRODUCTIVE FUSANT STRAIN

FIELD OF THE INVENTION

The present invention relates to a microbial process for making a highly productive fusant of *Tolypocladium inflatum*, a producer strain of cyclosporin A with immunosuppressive property and more particularly, to a method of producing cyclosporin A by submersed fermentation method comprising the steps of; Based upon a wild strain *Tolypocladium inflatum* which produced a small amount of cyclosporin A, developing amino acid-dependent mutant strain induced by UV radiation; conjugating other two amino acid-dependent mutants; making a highly productive fusant strain of cyclosporin A in parallel with increasing demanding of amino acid and organic nitrogen-source; and establishing the suitable condition and method of culture to these fusant to obtain the cyclosporin A by submersed fermentation method.

DESCRIPTION OF THE PRIOR ART

In more detail, *Tolypocladium inflatum* Gams NRRL 8044, a producer strain of cyclosporin A, is fungus and cyclosporin A which this strain produces is cyclic peptide consisting of 11 amino acids and molecular weight is 1,201, molecular formula is $C_{62}H_{111}N_{11}O_{12}$, and there are 25 derivatives according to variation of amino acids. [Traber R., HELVETICA ACTA, 70,13(1987)]

Cyclosporin A, of which chemical name is Cyclo[{(E)-(2S, 3R,4R)-3-hydroxy-4-methyl-2-(methyl-amino)-6-octenoyl}-L-2-aminobutyryl-N-methyl-glycyl-N-methyl-L-leucyl-L-valyl-N-methyl-L-leucyl-L-alanyl-O-ala nyl-N-methyl-L-leucyl-N-methyl-L-leucyl-N-methyl-L-valyl], is known to have antifungal, antiparasitic and antiinflammatory properties as well as a potent immunosuppressive property, and is important in the treatment of allograft rejection as well as autoimmune diseases[Borel 2 J. F., Prog. Allergy 38, 9 (1986)].

In general, the productive capacity of a producing strain is very important in producing secondary metabolites by fermentation of microorganisms.

*Sesquicillopsis rosariensis* G. ARNOLD F605 with 3150 mg/L and *Tolypocladium inflatum* Wb6-5 with 1100 mg/L (U.S. Pat. No. 5,256,547, 1993) are known as the highest productive strains among known cyclosporin A-producing strains.

The highly productive Cyclosporin A-forming strain among known strains has not been reported since cyclosporin A was for the first time isolated by A. Rueger et al. [Helv. Chem. Acta 59, 1075 (1976)], in-spite of the fact that the highly productive mutant of *Tolypocladium inflatum* has been developed actively and used as industrial producing strain.

SUMMARY OF THE INVENTION

The inventors made a highly productive cyclosporin A-forming mutant and invented a method for its fermentation. This mutant is characterized by producing cyclosporin A in high concentration, thus requiring large amounts of L-valine and L-leucine as well as organic nitogen source to produce cyclosporin A.

Cyclosporin A is cyclic peptide consisting of 11 amino acids; valine at position of 5, 11, leucine at position of 4, 6, 9, 10 and their derivatives. *Tolypocladium inflatum* NRRL 8044, a cyclosporin A-producing strain, has known to produce cyclosporines selectively by adding special amino acids, the structural constituents of cyclosporines to a culture medium [H.Kobel, European J. Appl. Microbiol Biotechnol 14:237–240, (1982)].

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

The inventors made the targeted fusant with amplified cyclosporin A-producing capability, where it comprises; as a method of amplifying production of cyclosporin A, mutating a poor producing strain of cyclosporin A, wild strain of *Tolypocladium inflatum* isolated from soil making L-valine-dependent mutant and L-leucine-dependent mutant, having a possibility to be precursor as constituent of target material, to amplify dependence on each amino acids; fusing the cells of two amino acid-dependent mutants to increase dependence on both L-valine and L-leucine.

Isolation of Cyclosporin A-Producing Wild Strain

Cyclosporin A-producing wild strain, *Tolypocladium inflatum* KD01, was isolated from soil collected at Mt. Chiri in Chollabuk-do, Korea.

Soil sample was cultured on a solid medium supplemented with a small amount of ampicillin to isolate fungi, from which family Moniliaceae including *Tolypocladium inflatum* was isolated by taxonominical characteristics of fungus. The strain with antifungal property against *Aspergillus niger* was selected from isolated strains of family Moniliaceae and then KD01 strain was selected from strains producing cyclosporin A corresponding with its pure product by TLC(Thin Layer Chromatography) and HPLC(High Performance Liquid Chromatography) analysis of their culture extract, identified as *Tolypocladium inflatum* with characteristics described as table 1 by a classified system of fungus.

Figure 1A:
FIG. 1A, 1B, and 1C are chromatograms of cyclosporin A, pure product and cyclosporin A produced by wild strain KD01 and the high-producing fusant KD461 of *Tolypocladium inflatum*, respecti vely.
Figure 1B:
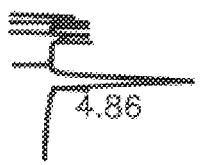
Figure 1C:
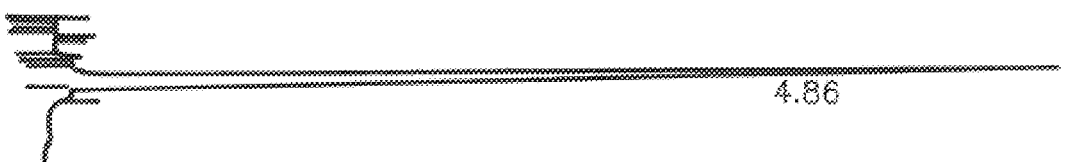

FIGS. 1A, 1B and 1C chromatograms are presented for cyclosporin A (pure product), cyclosporin A produced by a wild strain KD01 and the cyclosporin A high producing fusant, KD-461. In FIG. 1A the cyclosporin A (pure product) is represented by the main peak shown at 4.86 RT, its contents being over 98.5%. The cyclosporin A produced in the wild strain KD01 and the cyclosporin A high producing fusant, KD-461 are represented in FIGS. 1B and 1C, respectively, shown at 4.86 RT. The test conditions of the HPLC are those described in Example 1.

Isolated wild strain KD01 has low productivity of 175 mg cyclosporin A per liter. This strain has corresponding characteristics with *Tolypocladium inflatum* in terms of following; a) slow growth in a malt-yeast extract agar medium, b)formation of colony in white and with 5–6 mm of the diameter, c)no formation of sexual generation, d) formation of conidium with 1.8–3.0×1.4–2.0 μm, oval form, hyaline and scar, e)conidiophores with bulbous form at base, and f)arthrospores with oval form in a liquid medium.

TABLE 1

Identification of *Tolypocladium inflatum* and soil-isolated strain

|  | \Strain | |
| --- | --- | --- |
| Criteria for identification | *Tolypocladium inflatum* | Soil-isolated strain KD01 |
| I. Conidium | | |
| 1. Condidium is formed directly from hyphae | 0 | 0 |
| 2. Conidium isn't a coiled form | 0 | 0 |
| 3. Conidium and conidiopore are hyaline and bright color | 0 | 0 |
| 4. Typical conidium is a single cell with an oval form | 0 | 0 |
| II. Conidiophore | | |
| 1. Conidiophore has an apparent form | 0 | 0 |
| 2. Conidiophore is clearly distinguished from conidium | 0 | 0 |
| 3. Conidiophore is branched and phialides form in groups | 0 | 0 |
| 4. Lower portion of conidiophore is a bulbous form | 0 | 0 |
| III. Arthrospore | | |
| 1. Arthrospore is connected with segments | 0 | 0 |
| 2. Arthrospore is a rod from | 0 | 0 |

*H. L. Barnett, Illustrated Genera of Imperfect Fungi, Burgess publishing Co. Minneapolis, 1972

Selection of Amino Acid-Dependent Mutant

Spore suspension($10^9$/ml) of Tolypocladium inflatum KD01, a strain isolated from soil, was radiated by UV ray with the intensity of 300μ W/cm$^2$ for 90 seconds to induce mutation, culturing for 20 hours in a nutrient medium to germinate. Spores and hyphae were collected from culture and further cultured for 20 hours in a minimum medium with ammonium sulfate and ampicillin, of which final concentration is 20 mM and 3 mg/ml respectively, concentrating nitrogen source-dependent mutants. After this suspension was spread in a complete medium and cultured at 28° C. for 70 hours, appeared colonies were inoculated in minimum media and cultured at 28° C. for 7 days. When fungus unable to grow in a minimum medium was inoculated in a minimal medium supplemented with amino acid of lmM and cultured for 7 days, mutant strains, KD38 and KD94 which grew in a medium with L-valine or L-leucine, were obtained and identified as amino-acid-dependent strains on L-valine and L-leucine.

Preparation of Protoplast and Selection of Fusant

To prepare the -fusant of L-valine-dependent mutant KD38 and L-leucine-dependent mutant KD94 from selected amino acid-dependent strains, protoplast of each amino acid-dependent mutant was prepared first by modified method of Peberdy et al.[(Peberdy, J. E., J. Gen. Microbiol. 69:325–330, (1971)].

It was first performed to prepare protoplast of individual amino acid-dependent mutant, which it comprises; suspending fungi with biomass 50 mg/ml in solution containing cell-wall hydrolase, novozyme and cellulase, with individual concentration of 5 mg/ml, incubating at 28° C. for 3 hours for removal of fungal cell-wall, obtaining protoplast of $5 \times 10^8$/ml.

Protoplasts of KD38 and KD94 prepared in this way were mixed in equal amounts and fused in 30% solution of polyethyleneglycol containing calcium chloride of 0.01M and glycin of 0.05M at 30° C. for 10 minutes. It was regenerated by the following modified method of Anne et al. [(Anne, J., J.Gen. Microbiol. 92:413–417, (1976)]; smearing in a regeneration medium(3 g N—$NO_3$, 0.5 g KCl, 0.5 g $MgSO_4.7H_2O$, 0.01 g $FeSO_4.7H_2O$, 1 g $KH_2PO_4$, 40 g glucose, 0.7M NaCl, 2 g yeast extract, 18 g agar per liter), culturing at 28° C. for 5 days. Cell-fused strains, growing only in a medium with both L-valine and L-leucine, in frequency with 0.5 to 1.0% by plating regenerated fungi in a minimum medium, used in the selection of am)no acid-dependent strain, supplemented with L-valine, L-leucine and and both of them.

After spreading the fusant on a solid complex medium, culturing for 5 to 6 days and obtaining colony, a highly productive fusant strain with large inhibition-zone was selected by bioassay using *Aspergillus niger* as test-microorganism.

The second selection of fusant, first selected in this way, occurs in a liquid medium culture to select a highly cyclosporin A-producing fusant, where it comprises: a second submersed culture of fusant, selected by bioassay using *Aspergillus niger*, in a medium supplemented with L-valine and L-leucine, analysis of the extract of the broth by HPLC. Selected fusant not only require more L-valine and L-leucine but also improved the productivity of cyclosporin A to the level of 8,920 mg/L, showing results of fermentation as the following Table 3. The highly productive fusant of present invention(KD 461) is deposited in Korean Institute of Science and Technology on Mar. 7, 1994 under accession number KCTC 8556P. For the international patent application, it was converted the original deposit to a deposit under the Budapest Treaty in the Korean Institute of Science and Technology on Nov. 30, 1994 under accession number KCTC 0130 BP.

A highly cyclosporin A-producing fusant was made from soil-isolated strain KD01, identified as *Tolypocladium inflatum*, and its mycological characteristics were described in Table 2, compared with mother wild strain.

1. Characteristics in an Agar Medium

Figure 2:
FIG. 2 is a photographs showing a colonial morphology of wild strain KD01 and the fusant KD461 of *Tolypocladium inflatum* cultured in a malt-yeast extract medium, respectively.

The highly productive fusant KD461 of *Tolypocladium inflatum* KD01 directly isolated from soil has the following characteristics in comparison with originally occurring wild strain; slowly growing in a malt-yeast extract agar medium; forming somewhat small colony, forming less aerial mycelium, having irregular wrinkles in the surface of colony; and extruding in middle portion. While the surface of colony of wild strain is smooth and white with light yellow backside of medium, that of the fusant KD461 is light gray with dark brown backside of medium (as shown in FIG. 2).

while mycelium of wild strain is slender and elongate with thickness of 1–2 μm, less branched, with a needle-shaped head, that of the fusant is to some extent thick and short with thickness of 2–3 μm, swollen in the middle, more branched, with a head not being slender. Conidium of the fusant with about 1–2×10$^9$ CFU/ml, was less than that of wild strain with 2–3×10$^9$ CFU/ml.

TABLE 2

Comparison of mycological characteristics between soil-isolated strain. *Tolypocladium inflatum* KD01 and KD461

| Characteristics | Mother strain of *Tolypocladium inflatum* KD01 | Fusant *Tolypocladium inflatum* KD461 |
|---|---|---|
| 1. Morphology of colony | very short and elongate form of aerial hyphae with smooth and unfolded surface of colony | low frequency of aerial hyphae, condensed hyphae with irregular wrinkles in the surface of colony |
| 2. Size of colony (7 days) | 5–6 mm | 4–5 mm |
| 3. Color of colony | hyaline hyphae, white colony | light gray |
| 4. Color of backside | light yellow | dark brown |
| 5. Conidium | egg-shaped or oval form 1.5–2.0 × 2.0–2.5 μm | egg-shaped or oval form 1.0 –1.5 × 1.5 × 2.0 μm |
| 6. Conidiophore | conidiophore of apparent form with round shape in lower portion | conidiophore of apparent and branched form with round shape in lower portion |
| 7. Arthropore | oval form, 3–4 × 4–5 μm | 2–3 × 3–4 μm |
| 8. Production of cyclosporin A (mg/L) | 175 | 8920 |

2. Characteristics in a liquid nutrient medium

The wild strain in a liquid nutrient medium has the following characteristics; vigorous proliferation, slender and elongated hyphae, formation of stroma in a definite size, rapid formation of arthropores at 5–6 days of culture, production of cyclosporin A with gradual increase from 4 to 13 days of culture.

Figure 3A:
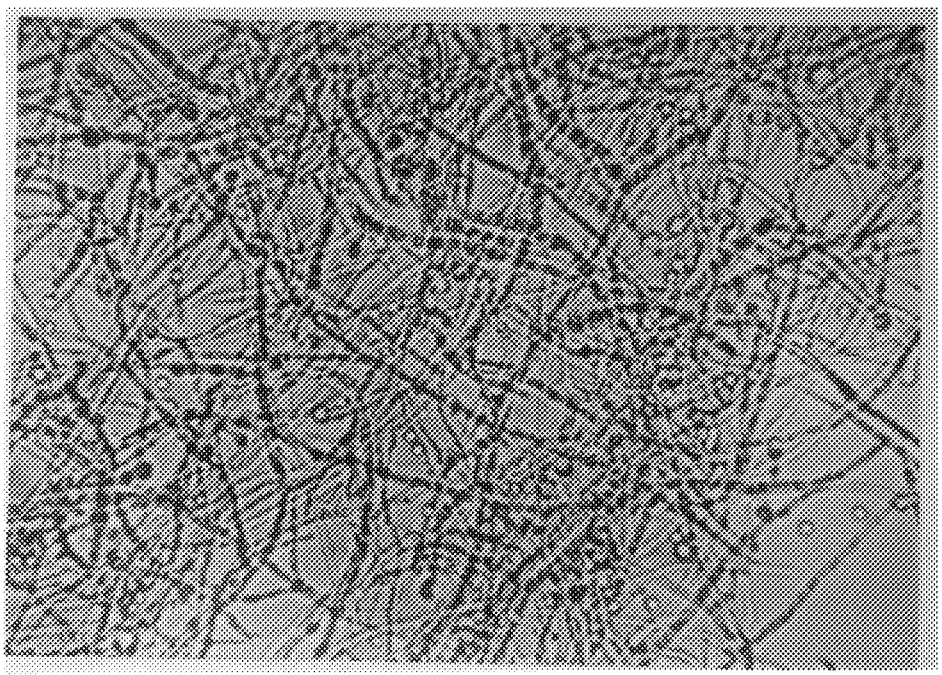
FIG. 3A and 3B are photographs (A) and (B) showing a morphology of hyphae, culturing wild strain KD01 and the fusant KD461 of *Tolypocladium inflatum* in a liquid culture medium for 192 hours, respectively.
Figure 3B:
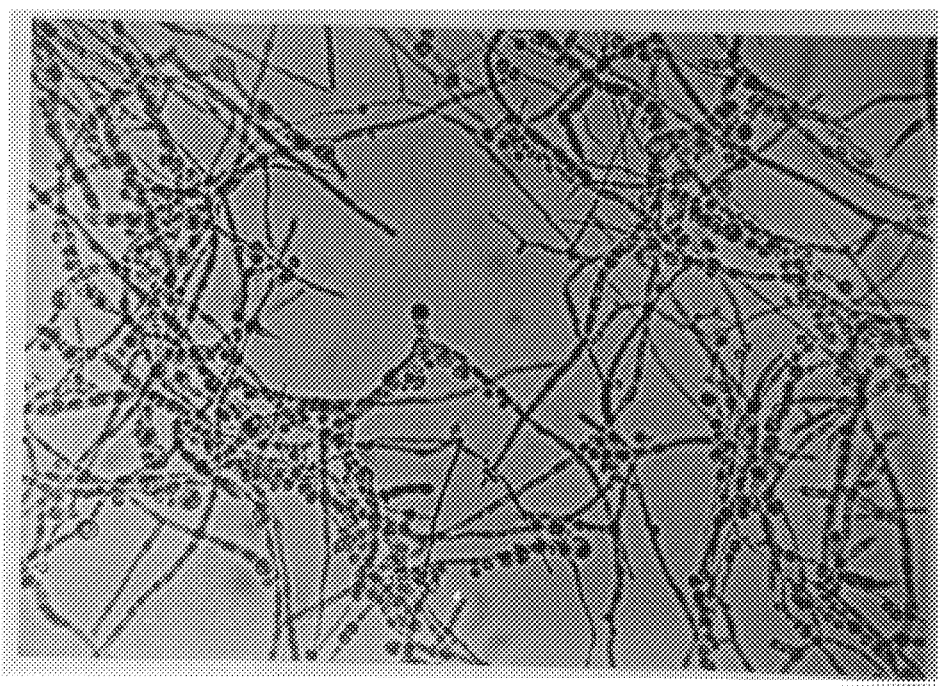

The fusant proliferates slowly more or less at early stage, with thick and short hyphae, many arthropores(as shown in FIG. 3). The production of cyclosporin A was shown to begin at 3 days and get to the maximum at 12 days in comparison with the wild strain.

While the culture medium of the wild strain was light yellow color, that of the fusant was dark brown.

3. The Productivity of Cyclosporin A

1) Increased requirement of L-valine and L-leucine for cyclosporin A production

Mother strain KD01 and the fusant strain KD461, conjugated with L-valine-dependent strain and L-leucine-dependent strain, were cultured in a nutrient medium, using glucose as carbon source and meat peptone as organic nitrogen source in various concentrations of L-valine and L-leucine, constituents of cyclosporin A. As a result, as shown in Table 3, the concentrations of L-valin and L-leucine were 4 g/L respectively for cyclosporin A maximal production whilst that of the fusant KD461 was increased up to 18 g/L, thus improving the production of cyclosporin A by 8920 mg/L. In other words, the fusant KD461 has recognized some unique properties in that it requires the large-scale amount of L-valine and L-leucine, precursor for the target compound and increases the production of cyclosporin A.

TABLE 3

Feature in production of cyclosporin A in mother strain and the fusant KD461 according to concentrations of L-valine and L-leucine

| Addition of amino acids (g/L) | | Production of cyclosporin A (mg/L) | |
|---|---|---|---|
| L-valin | L-leucine | Mother strain, KD01 | Fusant, KD461 |
| 1 | 0 | 45 | 1221 |
| 2 | 2 | 137 | 2180 |
| 4 | 4 | 175 | 3973 |
| 6 | 6 | 172 | 5810 |
| 10 | 10 | 170 | 7173 |
| 14 | 14 | 162 | 8379 |
| 18 | 18 | 131 | 8920 |
| 20 | 20 | 109 | 8159 |

2) Increase of the utility of organic nitrgen source

While mother strain KD01 requires mainly fine protein source such as peptone among many organic nitrgen sources for the production of cyclosporin A, a highly productive fusant KD461 has the increased proteolytic capability, in that it produces more amounts of cyclosporin A than known strain, using fine protein source like peptone as well as crude, cheap and natural protein sources like soybean meal, cottonseed meal, peanut meal and cornsteep loquor. Although the best organic nitrogen source is meat peptone, in the case of using as medium constituents in combination with peptone and natural organic nitrogen sources like soybean meal, the production of cyclosporin A is increased more than using only natural organic nitrogen source.

3) Comparison with the known cyclosporin A-producing strain

While the productivity of known cyclosporin A-producing strain has been to have 1100 mg/L of mutant wb6-5(IMET 43,899) of *Tolypocladium inflatum* and 3150 mg/L of mutant F605 of *Sesquicilliopsis rosariens* G. ARNOLD, the fusant KD 461 of present invention has high yield of 8920 mg/L(Table 4)

TABLE 4

Comparison productivity between known cyclosporin A-producing strain and the fusant KD461

| Producing strain | *Tolypocladium inflatum* ATCC 34921 | *Tolypocladium inflatum* wb6-5 | *Sesquicilliopsis ropsariens* G. ARNOLD F605 | Fusant, *Tolypocladium inflatum* KD461 |
|---|---|---|---|---|
| Basis | European J. App. Microbiol. | U.S. Pat. No. 5,256,547 | U.S. Pat. No. 5,256,547 | The Present Invention |

TABLE 4-continued

Comparison productivity between known cyclosporin A-producing strain and the fusant KD461

| Producing strain | Tolypocladium inflatum ATCC 34921 | Tolypocladium inflatum wb6-5 | Sesquicilliopsis ropsariens G. ARNOLD F605 | Fusant, Tolypocladium inflatum KD461 |
|---|---|---|---|---|
| | & Biotech 34, 513–517, 1982 | | | |
| Production of cyclosporin A (mg/L) | 710 | 1100 | 3150 | 8920 |

The invention is described in more detail by the Examples as set forth hereunder.

EXAMPLE 1

Strain: *Tolypocladium inflatum* KD461

Pre-culture medium: Glucose 40 g/L, Bactopeptone 20 g/L, Magnesium sulfate.$7H_2O$ 3 g/L, Ferrous sulfate.$7H_2O$ 0.01 g/L, Calcium phosphate 1 g/L, Potassium chloride 1 g/L, rice bran oil 1 g/L, pH 5.5

Producing medium: Glucose 120 g/L, Bactopeptone 20 g/L, Ammonium sulfate.$7H_2O$ 10 g/L, L-vaTine 18 g/L, L-leucine 18 g/L, Ferrous sulfate.$7H_2O$ 0.07 g/L, Zinc sulfate.$7H_2O$ 0.01 g/L, Cupric sulfate.$5H_2O$ 0.0005 g/L, Manganese chloride 0.002 g/L, pH 4.0–4.5

Culture-condition: Spore suspension, collected after incubation in a malt-yeast extract agar medium, is inoculated in pre-culture medium and cultured at 28° C. with 220 rpm in a rotatory shaker. 10% portions of culture are used to inoculated in a main medium and cultured at 28° C. for 13 days with 220 rpm in a rotatory shaker.

Analysis of the production: It was preformed as the following processes; mixing for 13 days cultured broth, 2N-Sodium hydroxide solution and Butylacetate at the rate of 1:1:2; extracting, separating solvent layer, vacuum drying; dissolving in mobile phase, analysis by HPLC, of which example is shown in FIG. 1C. The volumetric productivity of cyclosporin A by the fusant is 8920 mg/L.

Conditions for HPLC

Column: Develosil C8-3 (3 μm, 4.6×75 cm)

Mobile phase: D.W.: ACN=30:70

Temperature: 75° C.

Flow rate of mobile phase: 1.0 ml/min

EXAMPLE 2

Strain and pre-culture medium are the same as in Example 1, using bactopeptone 10 g/L and cornsteep liquor 10 g/L instead of bactopeptone 20 g/L in a main medium, yielding cyclosporin A of 8010 mg/L.

EXAMPLE 3

Strain and pre-culture medium are the same as in Example 1, performing pre-culture in a 7 L round-bottomed flask and main culture in a 30 L fermentor. The culture in fermentor occurs in the condition of temperature, of 28° C., aeration of 1VVM, stirring at 500 rpm, period of 10 days. The yield of cyclosporin A was 7980 mg/L.

EXAMPLE 4

Strain and pre-culture medium are the same as in Example 1, performing a first pre-culture in a 7 L round-bottomed flask and a second pre-culture in the same pre-culture medium in a 30 L fermentor and main culture in a 250 L fermentor at 28° C., aeration of 1VVM, stirring at 300 rpm for 10 days. The yield of cyclosporin A was 7710 mg/L.

We claim:

1. A fusant KD461 (KCTC 0130BP) comprising an L-valine-dependent mutant and an L-leucine-dependent mutant strain of *Tolypocladium inflatum*, said fusant having amplified cyclosporin A production.

2. The fusant of claim 1 wherein the amplified cyclosporin A production is a result of making the strain of *Tolypocladium inflatum* dependent on L-valine and L-leucine and by applying an organic nitrogen source.

3. A process for producing a fusant of claim 1 comprising: isolating a wild strain of *Tolypocladium inflatum*; irradiating said strain with U.V. rays so as to produce a mutant strain; culturing said mutant strain and supplementing said culture with amino acids , L-valine and L-leucine so as to produce strains which are dependent on L-leucine and L-valine; obtaining said amino acid dependent strains and fusing said strains.

4. The process of claim 3 wherein said culture is supplemented with an organic nitrogen source.

5. A process for manufacturing cyclosporin A by fermenting and cultivating a fusant KD461, said fusant comprised of an L-valine and L-leucine dependent strain *Tolypocladium inflatum*.

* * * * *